(12) United States Patent
Nazirizadeh et al.

(10) Patent No.: US 9,730,788 B2
(45) Date of Patent: Aug. 15, 2017

(54) DEVICE FOR OPTICALLY REPRESENTING INTRAOCULAR PRESSURE, AND A METHOD FOR SAME

(71) Applicant: Christian-Albrechts-Universitaet zu Kiel, Kiel (DE)

(72) Inventors: Yousef Nazirizadeh, Wiesbaden (DE); Martina Gerken, Kiel (DE); Torben Karrock, Bosau (DE); Johann Roider, Kiel (DE)

(73) Assignee: Christian-Alberts-Universitaet zu Kiel, Kiel (DE)

(*) Notice: Subject to any disclaimer, the term of this patent is extended or adjusted under 35 U.S.C. 154(b) by 27 days.

(21) Appl. No.: 14/406,827

(22) PCT Filed: Jun. 12, 2013

(86) PCT No.: PCT/DE2013/100214
§ 371 (c)(1),
(2) Date: Dec. 10, 2014

(87) PCT Pub. No.: WO2013/185757
PCT Pub. Date: Dec. 19, 2013

(65) Prior Publication Data
US 2015/0157453 A1 Jun. 11, 2015

(30) Foreign Application Priority Data
Jun. 13, 2012 (DE) .................. 10 2012 105 129

(51) Int. Cl.
*A61B 3/16* (2006.01)
*A61F 2/16* (2006.01)

(52) U.S. Cl.
CPC ............ *A61F 2/1613* (2013.01); *A61B 3/16* (2013.01); *A61F 2/16* (2013.01); *A61F 2/1659* (2013.01);
(Continued)

(58) Field of Classification Search
USPC .......................................... 600/398
See application file for complete search history.

(56) References Cited

U.S. PATENT DOCUMENTS

2004/0254438 A1* 12/2004 Chuck .................. A61B 3/16
600/398
2009/0299216 A1 12/2009 Chen et al.

FOREIGN PATENT DOCUMENTS

DE 102005041271 A1 3/2007
WO 2004062480 A2 7/2004
(Continued)

OTHER PUBLICATIONS

International Search Report dated Oct. 1, 2013, International Application No. PCT/DE2013/100214.

*Primary Examiner* — David H Willse
*Assistant Examiner* — Javier Blanco
(74) *Attorney, Agent, or Firm* — Stephen A. Pendorf; Patent Central LLC

(57) ABSTRACT

A device for optically representing intraocular pressure, having an arrangement which is implanted into the eye with a membrane that curves outwards when the intraocular pressure changes, and a contact surface, these altering the polarization for a spectral range of incident and reflected light in the region of their contact with one another, as well as a read-out arrangement that optically reproduces a planar image of the light which is reflected by the photonic crystal and whose polarization has been altered, and that comprises a polarization filter for the irradiated light and the light reflected by the photonic crystal. Also, a method for measuring intraocular pressure.

3 Claims, 2 Drawing Sheets

Figure 1:
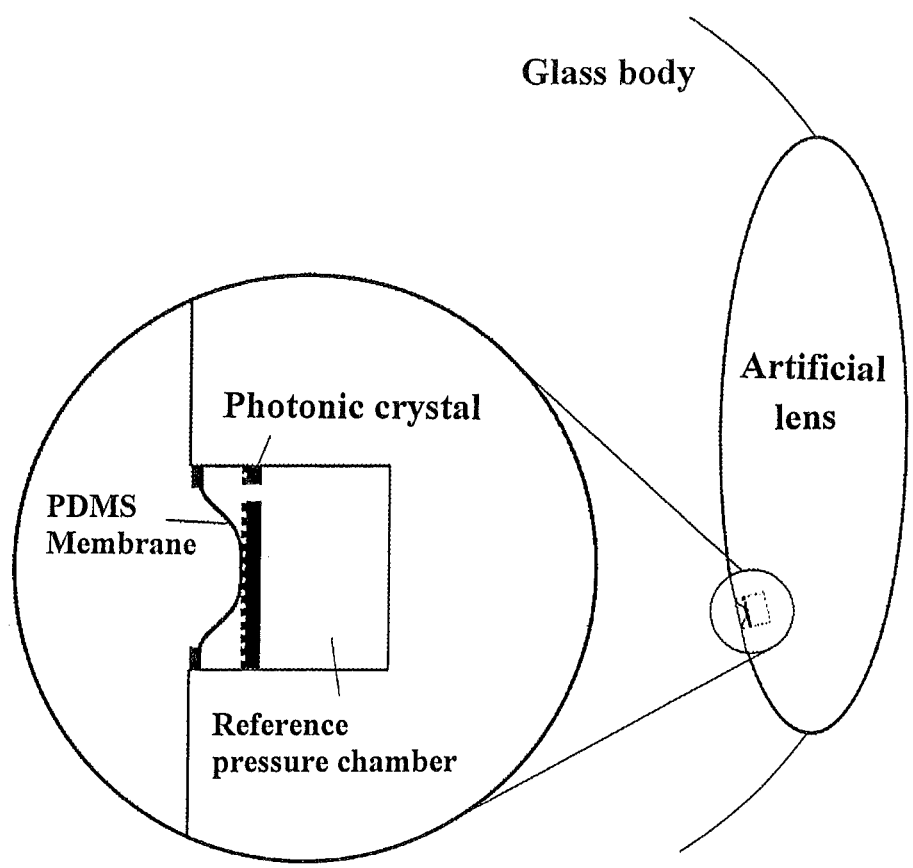

(52) U.S. Cl.
CPC ............. *A61F 2002/1699* (2015.04); *A61F 2002/16965* (2015.04)

(56) References Cited

FOREIGN PATENT DOCUMENTS

| WO | 2007035356 A2 | 3/2007 |
|----|---------------|--------|
| WO | 2010100654 A2 | 9/2010 |
| WO | 2011082314 A2 | 7/2011 |

\* cited by examiner

DEVICE FOR OPTICALLY REPRESENTING INTRAOCULAR PRESSURE, AND A METHOD FOR SAME

The invention relates to a device according to the preamble of the main claim for the optical representation of the intraocular pressure.

As part of cataract surgery about 650,000 intraocular lenses are implanted in Germany annually.

The increased intraocular pressure is, in pathogenesis, one of the main reasons for glaucoma, which can cause loss of vision or field of vision. The number of occurrences of blindness from glaucoma is estimated at about 50,000 per year. However, timely measurement of intraocular pressure and appropriate drug treatment and timely surgical therapy could prevent succumbing to the condition.

However, the current methods are unpleasant due to requiring contact with the patient's eye, and also are not very meaningful, since they measure the internal pressure only indirectly by measuring tension of the outside of the eye. Usually this is done by applanation tonometry, in which an impression of the cornea takes place by contact. Since this is unpleasant, it has the consequence that the intraocular pressure measurements are carried out only at select points in time, for example, only a few times a year. As a result, only some of the glaucoma patients will even be diagnosed timely.

A gentle method in which the deformation of the cornea is measured in response to an air blast provides only inaccurate results.

It is therefore desired that a patient be able to determine his intraocular pressure using a small, preferably automated, readout device automatically and without touching.

It is therefore an object of the invention to provide an externally readable intraocular pressure sensor for reading by either the patients themselves or, with higher accuracy, at pharmacies or by medical personnel.

In the simplest variant, a purely visual measurement is performed using a special magnifying glass, in which the patient determines the size of the color circle of the sensor.

The process of the invention for the optical representation of the intraocular pressure will work with a device preferably implanted on an intraocular lens in the eye, with a membrane which bulges with changing intraocular pressure and a contact surface. With an increase of the intraocular pressure, there occurs in the area of the contact of the membrane with the contact surface, for example, by a reversible chemical reaction in the region of contact or by other optical effects, a change in the polarization of one spectral range of the incident and reflected light.

A readout device for optical reproduction of a two-dimensional image of the light reflected from the photonic crystal and changed in polarization, which has a polarization filter for the light radiated onto and reflected from the photonic crystal, can work with natural light for the purely visual measurement, and be comprised of for example a mirror, with which the patient directs light into the eye himself. In front of the mirror, a circular polarizing filter would be provided, which polarizes the incident and also the back-reflected light. The observation of the eye would be made by the patient in the mirror, wherein he would see no or small discolored area as indication of normal intraocular pressure.

In particular, it is proposed for affecting change in polarization, to make the membrane to be deflected onto an adjacent nanostructured surface of a photonic crystal which is fixed in the intraocular lens and optically transparent to the wearer, so that the membrane rests with elevated intraocular pressure on a planar surface on the nanostructured surface. For better configuration of a characteristic curve, this surface may also be formed dome shaped. It is also possible to imprint a plurality of contact points or rings on this surface to give a stepwise progressive change to the presentation.

Finally, it would also be possible to provide a defined reference scale on the pressure surface with a known geometric dimensions, or an already existing bar code or ID number can be moved so close to the area of contact between the membrane and surface that, particularly in the case of a camera and software evaluation, it the surface of the reference scale appears in the image.

As for an automated reading device, it is proposed to operate with a defined illumination and to provide a camera as part of the read-out device, wherein a storable image is produced. In this embodiment, two longitudinally polarizing filters may be provided, one in the incident light and the one in the reflected light are crossed by 90°, for representing the area of the contact surface as the difference image.

The camera captured image can then be processed with computer means using a known reference value contained in the image for the determination of a quantified value of the intraocular pressure from the size of the detected contact area.

Finally, the invention proposes that the nanostructured surface is situated within a reference pressure chamber, which is closed off by a membrane, is provided in the intraocular lens, of which the internal pressure is measured in a manner, such that at normal ocular pressure there exists no or only minimal contact between the membrane and the surface.

Figure 2:
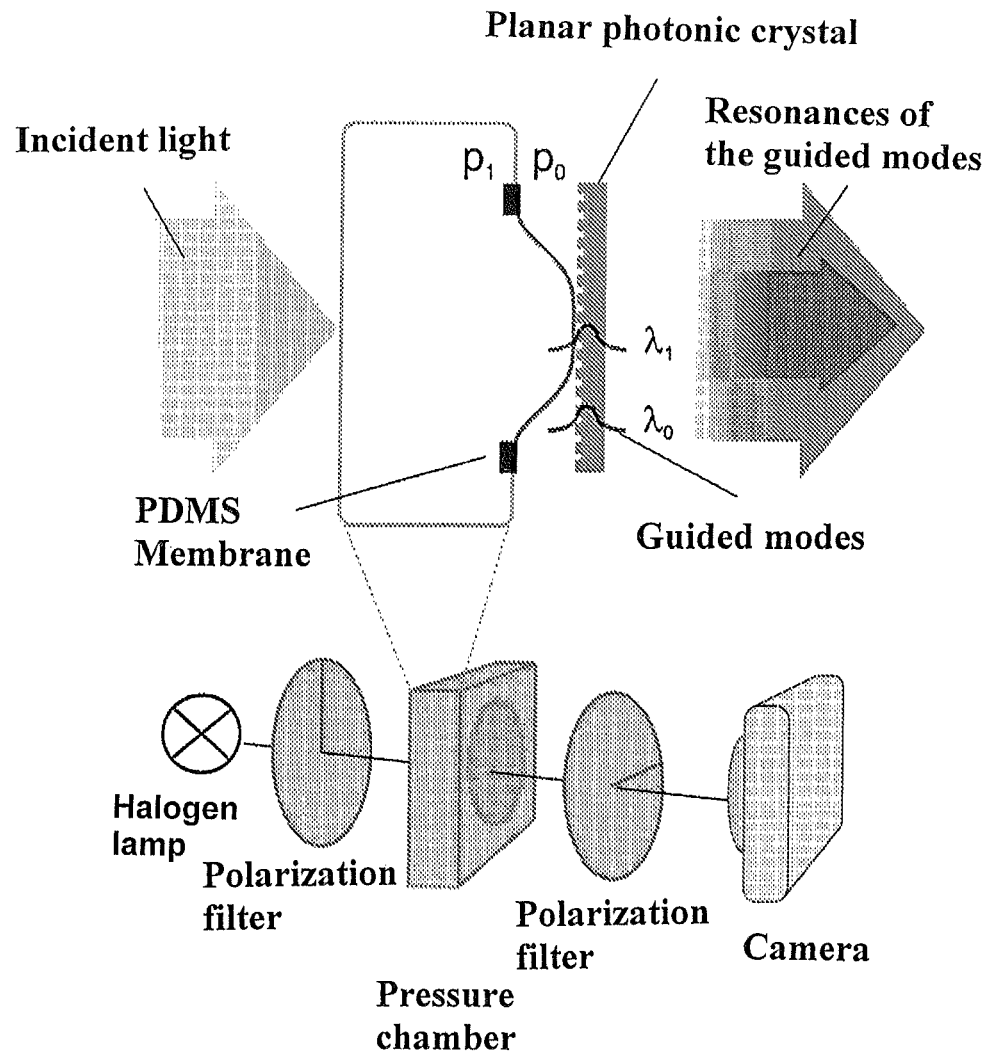

Further features and advantages of the invention will become apparent from the following description of a preferred embodiment. Therein:

FIG. 1 is a schematic representation of an artificial lens with a built-in intraocular pressure sensor at an edge, and FIG. 2 shows a measurement set-up for reading the pressure value in the form of a larger or smaller visible surface depending on the pressure.

As shown in FIG. 1, the intraocular pressure sensor is comprised of a movable membrane, a periodically nano-structured surface (photonic crystal) and a reference pressure chamber. The reference pressure is pre-set such that at the lowest intraocular pressure value the membrane just touches the photonic crystal surface. It is conceivable, in consideration of the various possible intraocular pressures, to provide a set of artificial lenses, each with different reference pressure, so that during the implantation a lens appropriate for the patient can be used.

With an increase in pressure in the eye, the membrane is then pressed over a wider area of the photonic crystal. The reflection spectrum is different locally, depending on whether the membrane is pressed against the photonic crystal or not, since the pressed-against membrane leads to a refractive index change at the surface of the photonic crystal.

During readout of the sensor with a broadband light source (visible light, daylight), this results in a different color appearance in areas pressed against by the membrane. For example, the area may appear red with pressed-against membrane, while the remaining surface appears yellow. If the pressure changes, so does the size of, for example, a red circle and simultaneously this area takes over coloring of more of the remaining area.

FIG. 2 shows a measurement set-up for reading the pressure value in the form of a visible surface which becomes larger or smaller depending on the pressure.

The invention claimed is:

1. An apparatus for optical representation of intraocular pressure, the apparatus comprising:
    an intraocular pressure sensor mounted within an intraocular lens (IOL), the intraocular lens adapted to be implanted in an eye, wherein the intraocular pressure sensor includes a reference pressure chamber having:
        a membrane which bulges with changing intraocular pressure when implanted in the eye, the membrane being optically transparent, and
        a contact surface comprising a photonic crystal having a periodically nanostructured surface situated within the reference pressure chamber, wherein the membrane is deflectable out onto the periodically nanostructured surface of the photonic crystal when the membrane bulges with changing intraocular pressure, whereby in the area of contact between the membrane and contact surface a change in a spectral range of incident light and reflected light is caused, and
    an external readout device adapted to be used with the intraocular pressure sensor, the readout device including a circular polarization filter in the path of incident light and a circular polarization filter in the path of the light reflected by the photonic crystal,
    wherein when the membrane contacts the photonic crystal, it causes the light which is reflected by the photonic crystal to be altered in polarization,
    wherein the readout device optically reproduces a planar image of the light which is reflected by the photonic crystal and whose polarization has been altered, and
    wherein the circular polarization filter in the path of incident light and the circular polarization filter in the path of the light reflected by the photonic crystal are crossed by 90°, to represent the area of the contact surface as a difference image.

2. The apparatus according to claim 1, wherein a camera is provided as part of the readout device, whereby a storable image is produced.

3. The apparatus according to claim 2, wherein a camera image is produced and the camera image is then processed with computer means using a known reference value contained in the image for the determination of a quantified value of the intraocular pressure from the size of the detected contact area.

* * * * *